United States Patent [19]

Castellini

[11] Patent Number: 5,022,858
[45] Date of Patent: Jun. 11, 1991

[54] PORTABLE DENTAL INSTRUMENT STERILIZING CONTAINER

[75] Inventor: Franco Castellini, Bologna, Italy

[73] Assignee: Castellini, S.P.A., Bologna, Italy

[21] Appl. No.: 265,392

[22] Filed: Oct. 31, 1988

[30] Foreign Application Priority Data

Nov. 18, 1987 [IT] Italy ................... 5002/87[U]
Jul. 6, 1988 [IT] Italy ................... 4880/88[U]

[51] Int. Cl.⁵ .......................................... A61C 17/14
[52] U.S. Cl. ............................................ 433/97; 433/77
[58] Field of Search ................................... 433/97, 77

[56] References Cited

U.S. PATENT DOCUMENTS 1,537,140  5/1925  Russell et al. .................. 433/97
4,545,956  10/1985  Ciszewski et al. ................ 422/28

FOREIGN PATENT DOCUMENTS 2459881  6/1976  Fed. Rep. of Germany ........ 433/97
3246266  6/1984  Fed. Rep. of Germany .
3611327  8/1987  Fed. Rep. of Germany .

Primary Examiner—Gene Mancene
Assistant Examiner—Adriene B. Lepiane
Attorney, Agent, or Firm—Laff, Whitesell, Conte & Saret

[57] ABSTRACT

A portable dental instrument sterilizing container adapted to be connected to a support which flanks a dental chair. The container has a top section, an internal middle section and a bottom section. The bottom section has a projection adapted to be inserted into a well formed in the support. The top section has a plurailty of holes to form dental instrument holding sockets. A portion of the top section is shaped so as to rest a drinking cup thereon. The middle section forms an internal container that is in communication with the sockets. The internal container has a suction port, a drainage port and sized such that the dental instruments within the sockets, project above the top section.

7 Claims, 3 Drawing Sheets

PORTABLE DENTAL INSTRUMENT STERILIZING CONTAINER

BACKGROUND OF THE INVENTION

The invention relates to a portable dental instrument sterilizing container. The container collects and disposes of the soiled liquids ejected from dental surgery instruments during or following sterilization of their internal passages. The container holds the instruments during such operations. The prior art embraces apparatus for sterilizing the air and/or water supply passages of the handgrips of certain dental surgery instruments such as high speed drills and scale removers. The fluids supplied through these passages serve as propellant for the instrument and/or as coolants for the instrument while being used in the area of the patient's mouth subjected to treatment. Apparatus of the type in question is disclosed in DE-OS 3 246 266. This discloses that at a convenient moment when the instruments are not in use, the instruments are placed in the sterilizing apparatus. The internal passages of the instruments are filled to capacity with a sterilizing liquid. The sterilizing liquid is left to act for a given duration before being ejected forcibly from the passages, generally by flushing out with water. In fact, these instruments form part of a column-mounted assembly of equipment to be found in any modern dental surgery equipment which incorporates a pressurized supply of water for their operation. Turning on the water supply, the internal passages of the instruments are flushed clear of the soiled sterilizing liquid and rinsed and filled with clean water in the process. Thus, with the rinse completed, the passages remain primed with water in readiness for subsequent use. When carrying out the two operations of sterilizing and flushing the passages, splashing and dripping are prevented by placing the instruments initially in a special container. The special container serves ultimately to collect the sterilizing liquid and with it, the substances removed from the passages. Care also needs to be taken to ensure that the sterilizing liquid, an acid and chemically aggressive fluid in most cases, will not overflow from the container. Such overflow would stain, if not actually damage the surface on which the container stands. Accordingly, the volume of the container will be such, preferably, to accommodate the entire quantity of sterilizing liquid and flushing liquid utilized. Further, provision must be made to ensure that the instrument grips will not fall and become dirty, and/or cause the surface on which the container stands to be subjected to chemical attack.

German patent DE PS-36 11 327 discloses apparatus in which to place the handgrips of dental surgery instruments and collect the soiled sterilizing liquid aforementioned. The apparatus can be positioned over the spittle bowl of the column equipment and discharge its contents thereinto from an annular chamber, or trap, that forms part of the container. This type of apparatus permits a continuous discharge of any sterilizing liquid overflowing from the trap to the spittle bowl. However, whilst the overflow problems are eliminated by such an arrangement, absolute hygiene cannot be guaranteed in that the spittle bowl is a ready source of germs. An additional drawback of the trap-type apparatus is that the instruments and their handgrips are held permanently in an environment (the annular chamber) that is also occupied by the soiled sterilizing liquid, and inevitably, by the germs entrained in it. Another problem arising with the German patent apparatus is that of the difficulty experienced with cleaning operations. The annular chamber has to be upturned in order to empty it entirely of its contents. This is a contingency that necessarily influences the mobility and positioning of the container. The annular chamber serves additionally to enable part immersion in the soiled sterilizing fluid, of the terminal section of the instrument and of the end of the suction tube connected to the column vacuum pump. However, as the suction capacity of this tube is distinctly greater than the capacities of the various instruments and handgrips put together, the need also exists for a replenishing system to keep the annular chamber topped up with liquid to ensure that it will not empty out and cause the suction tube to draw in air only. With the container placed above the spittle bowl, the empty chamber will be in direct communication with the outlet of the bowl. Accordingly, the object of the present invention is to overcome the drawbacks described above.

SUMMARY OF THE INVENTION

The stated object is achieved with a portable dental instrument sterilizing container. The container is adapted to be placed in the sunken holder or well incorporated into surgery equipment columns that accommodate the drinking glass used by patients for oral rinsing purposes. According to the invention, the container is provided with at least one outlet that discharges the soiled sterilizing liquid directly. That is, without being allowed to accumulate, and discharging at least into the outlet of the sunken drinking glass holder. A further object of the invention is to provide a container that will allow continued use of the entire equipment column even while sterilization and/or disinfection of instruments is in progress. This is achieved by having a lowered profile in the uppermost surface of the container, located substantially above a projection that fits into the sunken drinking glass well of the existing equipment column. The lowered profile incorporates a similar well for accommodation of the drinking glass and an outlet hole. With the container in its operating position, the outlet hole is vertically aligned with the overhanging spout of a water tap serving to replenish the drinking glass.

One advantage of the invention is essentially one of efficiency and safety. This is gained by virtue of the various outlets afforded by the column. The outlet of the drinking glass well is without doubt the least prone to contamination by germs.

Another advantage of the invention is that of the level of hygiene obtainable. The sterilizing liquid flushed from the instruments is discharged from the container continuously and directly, without being allowed to accumulate.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
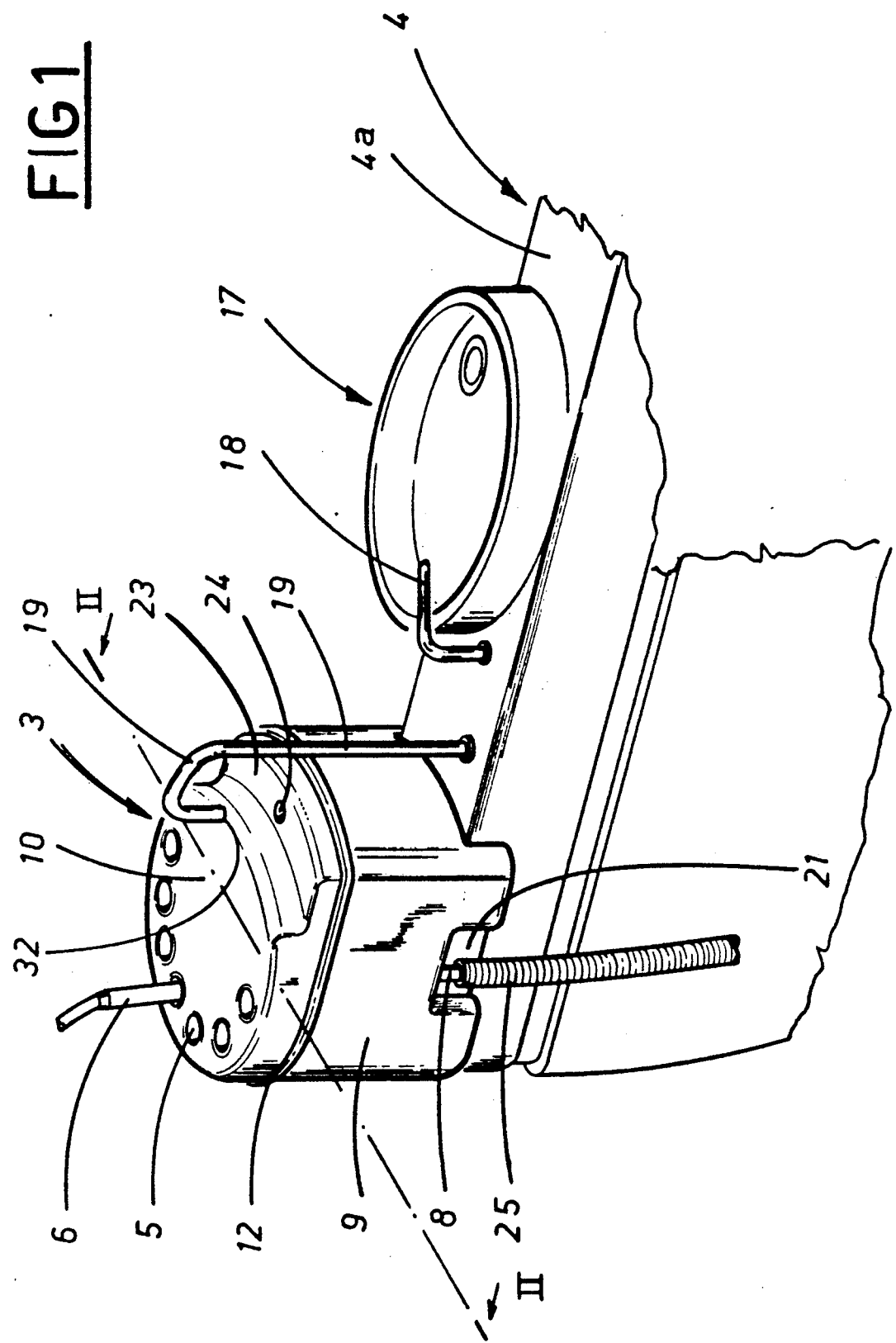
FIG. 1 shows a perspective of the container disclosed, seen fitted to a dental surgery equipment column and holding an instrument for sterilization.

Observing FIG. 1, the portable dental instrument sterilizing container 3 rests on a support 4a afforded by the equipment column 4 with which the surgery instruments 6 for sterilization are associated.

Figure 2:
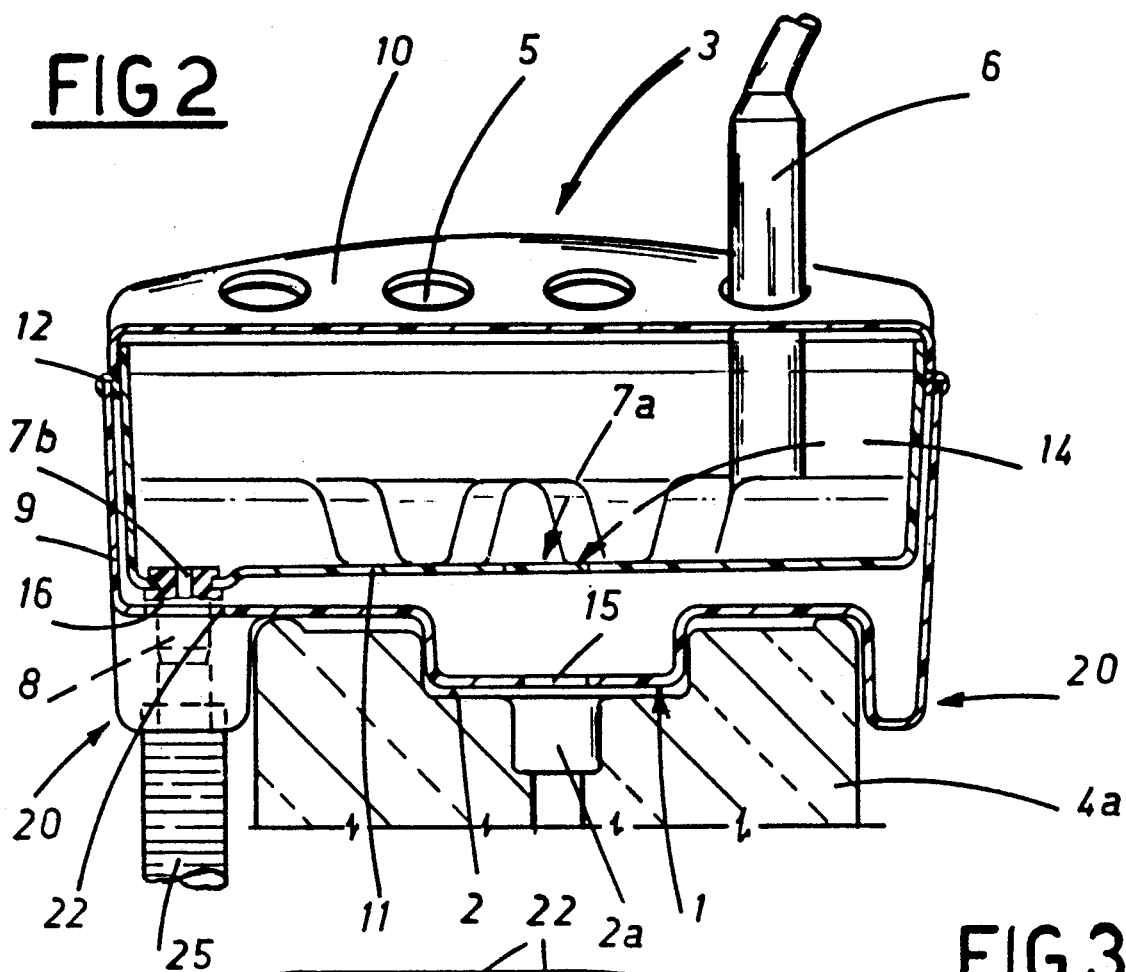
FIG. 2 illustrates a partial cross-sectional view of the container of FIG. 1 taken along lines II—II.

The support 4a forms a part of that section of the column 4 flanking the chair occupied by the patient. The column 4 incorporates, amongst other items, a spittle bowl 17, a nozzle 18 from which water is dispensed into the bowl for cleansing purposes, and a sunken holder or well 2 (FIG. 2). The well 2 serves as a stand for a drinking glass (not shown in FIG. 1) holding water for the patient's oral rinse.

An arched water tap 19 projects from the support 4a. The overhanging spout 32 is directed down into the well 2 so as to permit refilling of the drinking glass.

The bottom of the well 2 has an outlet hole 2a, connected with the main waste outlet of the column 4. This serves to drain off any water dripping from the tap 19 or overflowing from the drinking glass.

The container 3 according to the invention has a projection 1 at its bottom to be inserted into the well 2 defined by the support 4a (see FIG. 2). The container is provided uppermost with a plurality of sockets 5 in which to position the instruments 6 for sterilization. The container has a bottom outlet 7 (FIG. 2) from which liquids are discharged directly. That is, without first accumulating in the container.

The container 3 consists of three distinct parts: a hollow bottom section 9, a hollow top section 10, and a middle section. The top section and bottom sections are disposed with their hollow insides facing one another. Viewed in plan, the container 3 exhibits a shape that is substantially symmetrical in relation to a single axis coinciding with that of the support 4a. Accordingly, there is only one way in which the three sections 9, 10 and 11 can be assembled. The projection 1 projects from the bottom section 9 substantially at center. The projection is flanked on either side by bottom projections 20 that embrace the support 4a to ensure that the container 3 has greater stability. This is particularly helpful when instruments 6 are placed in the respective sockets 5 for sterilization.

A hole 15 is formed in the projection 1. The hole 15 is located in alignment with the outlet 2a of the drinking glass well 2 in the support 4a.

A recess 21 is formed in one of the two side projections 20 of the bottom section 9 (FIG. 1). The uppermost surface of the recess defines one or two openings 22 (FIG. 2) serving to accept the relative couplers 8 of suction tubes 25 connected to the vacuum pump of the column equipment. One of these openings 22 can be used in place of the outlet hole 15 aforementioned.

Figure 3:
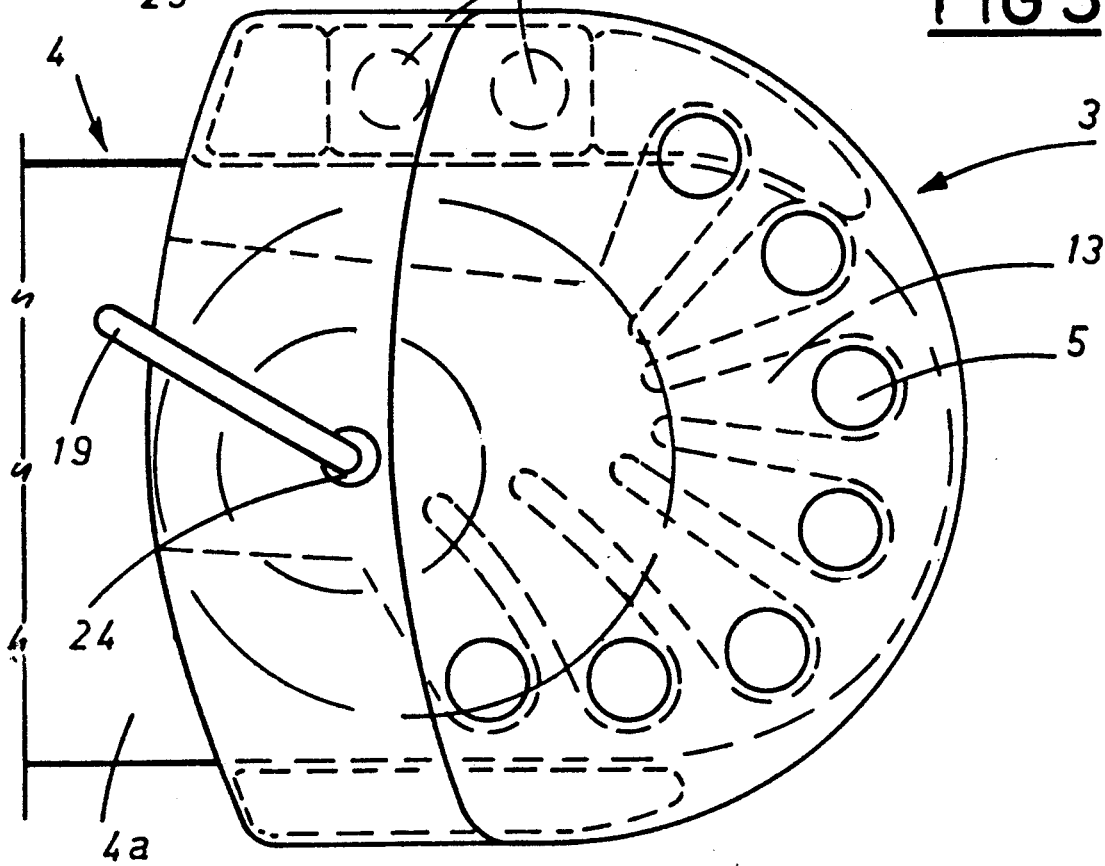
FIG. 3 shows a plan view of the container of FIGS. 1 and 2, in which no instruments are shown.

The top section 10 of the container will be seen to define a plurality of holes that combine with the middle section 11 in a manner that will hereinafter become clear. The holes create the sockets 5 in which the instruments 6 for sterilization are accommodated. The top section 10 also has a slightly lowered profile 23 adjacent to the water tap 19. The lower profile 23 has a hole 24 located in vertical alignment with the spout 32 of the tap 19 (FIGS. 1 and 3). Thus, in the event of the tap dripping, water will be prevented from trickling over the container 3 and down onto the support 4a or to the floor.

The internal middle section 11 of the container is embodied substantially as a basin that fits into the bottom section 9 and is covered by the top section 10. The base of the middle section also serves as a depth stop to check the descent of the instruments 6. A seal 12 is located between the top and middle sections 9 and 11 to ensure a tight seal and, at the same time, to stabilize the fit between the two sections. The seal has an essentially C-shaped profile that envelops the top lip of the bottom section 9 and provides a surface on which the top section 10 can rest in fluid-tight contact.

The direct discharge outlet 7 referred to above is located in the base of the middle section 11. The outlet 7 may be located substantially in a central position as denoted by 7a in FIG. 2. Alternatively, the outlet is made to coincide with the bore 7b of a quick coupler or other fitting 8 inserted through and clamped to a hole 16 located at one side of the base. In this instance, the hole 16 will be aligned vertically with the opening 22 in the recess 21 in such a way that the coupler 8 can project downwards and be connected without difficulty to the end of the suction tube 25.

The base of the middle section 11 might be solid with a removable piece or knock-out 14 in a substantially central position to permit utilizing the suction line outlet 7b without opening up additional holes. Alternatively, the fitting 8 at the side outlet could be blocked, and the central outlet 7a then opened by applying pressure to the knock-out 14 and removing it from the base, to utilize the outlet 15 in the center of the bottom section 9.

The base of the middle section 11 will also define a plurality of channels 13 (FIG. 3) disposed in a substantially radial pattern, each terminating at a respective peripheral point directly beneath a corresponding socket 5 in the top section 10.

The channels 13 converge on the outlet 7a (or the knock-out 14). They have a depth such as to ensure that liquid ejected from one instrument 6 will not splash onto and pollute the instruments 6 occupying the adjacent sockets.

Finally, the base of the middle section 11 slopes gently toward the central and side outlets 7 and 16 (FIG. 2) in order to ensure that the soiled liquids drain off freely.

Operation of the device 3 will now be described, assuming that disposal of the soiled sterilizing and flushing liquids ejected from the instruments 6 is effected by way of the coupler 8.

Having selected the moment to effect sterilization, the container 3 is set on the support 4a. Care is taken to locate the bottom projection 1 faultlessly in the well 2 and line up the hole 24 of the top section 10 beneath the outlet 32 of the tap 19.

Figure 4:
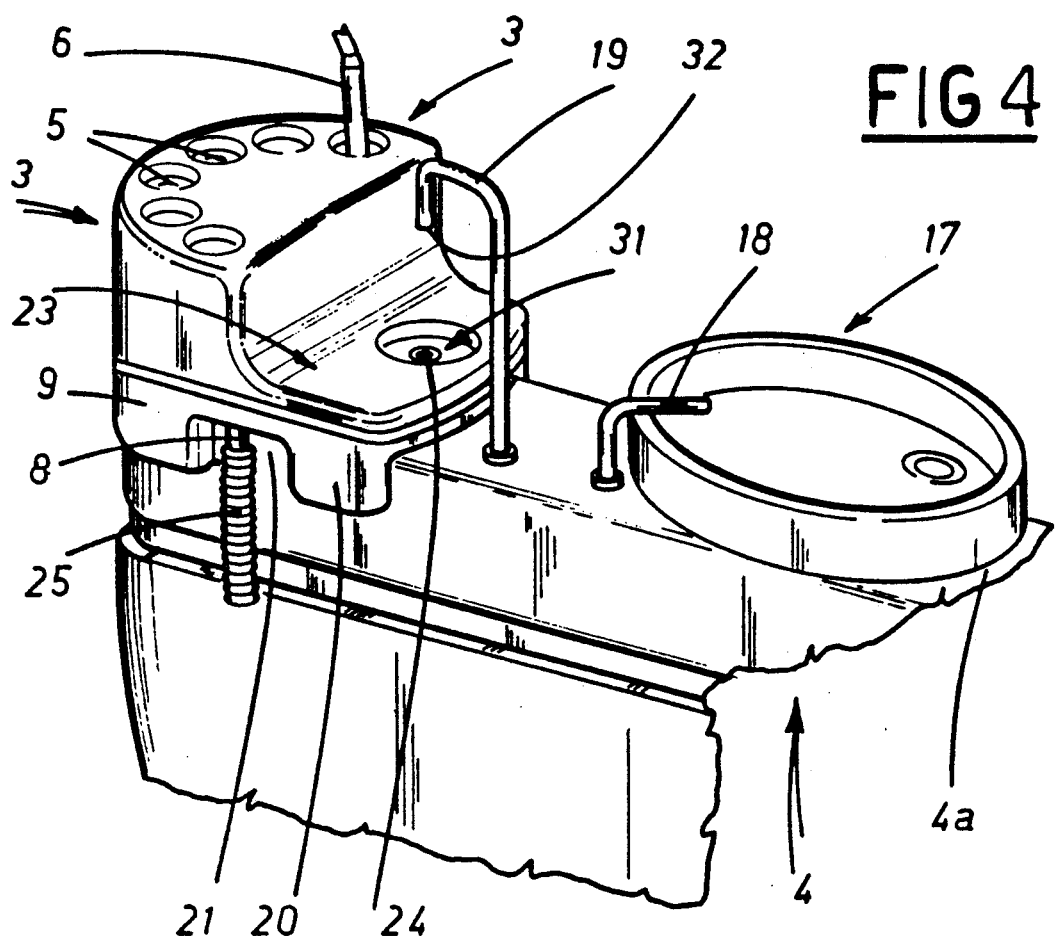
FIGS. 4 and 5 illustrate an alternative embodiment of the container seen in substantially the same views as FIGS. 1 and 2, respectively.
Figure 5:
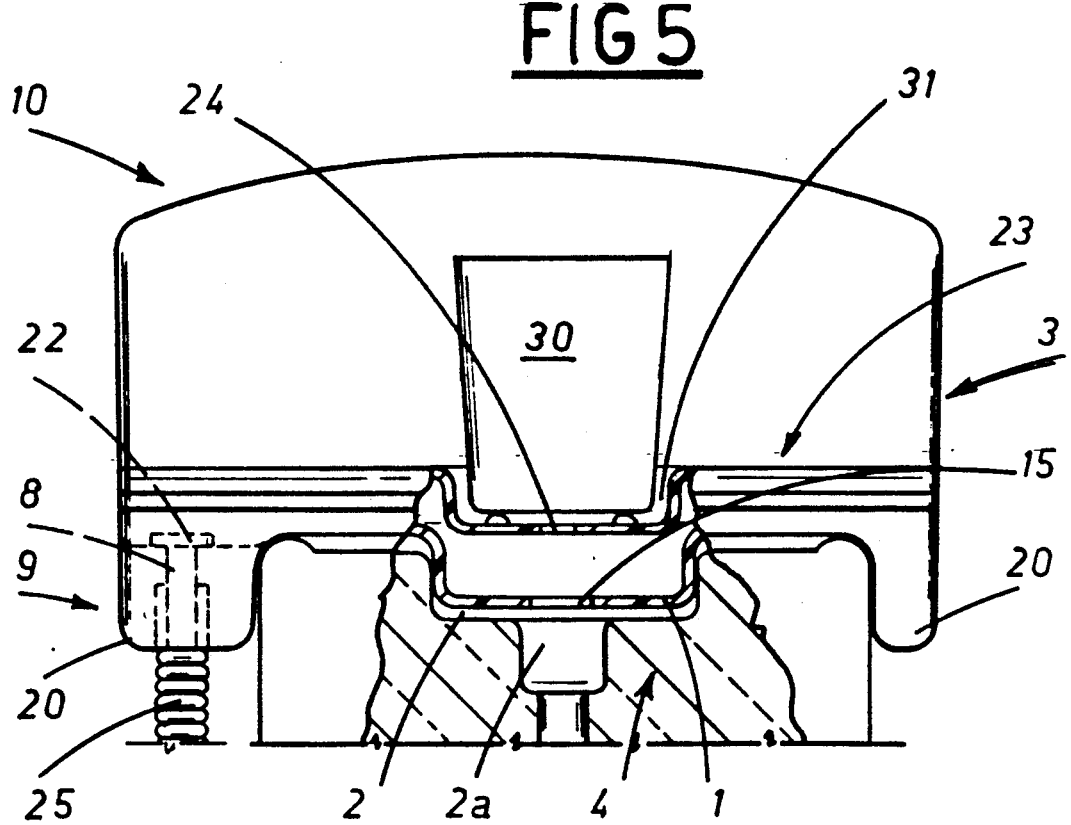

This accomplished, the suction tube or tubes 25 are connected to the coupler/s 8. The instruments 6 are placed in their relative sockets 5 and sterilization can commence. The vacuum pump is also switched on. Accordingly, the soiled sterilizing liquid ejected from the instruments 6 will fall into the channels 13 and run toward the outlet 7b, because of the gentle gradient. Thereafter, the soiled sterilizing liquid is discharged along the length of the tube 25 to join the main waste outlet of the equipment column. Sterilization completed, the same process is repeated with rinsing water. Should the user prefer not to utilize the suction tube 25 as an outlet, the coupler 8 can be blocked and the central outlet 7a utilized. In that case the soiled sterilizing liquid and the flushing liquid will discharge into the drinking glass well 2 and out via the main column outlet entirely unobstructed. Cleaning of the device is abundantly simple. With sterilization accomplished, the inside of the container will exhibit no more than a slight dampness left by the rinsing liquid. The soiled sterilizing liquid has been flushed from all internal surfaces including those of the channels 13. In an alternative embodiment illustrated in FIGS. 4 and 5, the lowered profile 23 is more pronounced compared to that of the embodiment illustrated in FIG. 1. This embodiment incorporates a well 31 for a drinking glass 30. The drip hole 24 is located in the well 31, in this instance, vertically aligned with the spout 32 of the water tap 19 (see FIG. 4), and preferably also aligned with the bottom outlet hole 15. Furthermore, the profile 23 is lowered sufficiently to permit accommodation of the drinking glass 30 beneath the spout of the water tap 19, even when the container 3 is positioned with its bottom projection 1 inserted in the well 2 of the column support 4a and operational.

With this embodiment, it becomes possible to leave the container permanently in position on the support 4a. The container 3 is in readiness for further sterilization and/or disinfecting operations while at the same time, retains the use of the drinking glass 30 for oral rinsing purposes. The container utilizes the well 31 afforded by the container in place of the permanent well 2 in the column support 4a.

The foregoing specification implies no limitation of scope. For example, the walls of the sockets 5 accommodating the instruments 6 might extend down toward the middle section 11 in a taper, rather than with the straight profile illustrated.

What is claimed:

1. A portable dental instrument sterilizing container which is to be connected to a support which flanks a dental chair with said support having a well defined in its top surfaces comprising:
    a top section, a bottom section and an internal middle section,
    said bottom section having a projection formed in its bottom surface which is sized and adapted to be inserted in said well to hold and stabilize said sterilizing container on said support,
    said top section having a plurality of holes therein which form dental instrument holding sockets,
    a portion of said top section being shaped to rest a rinsing cup therein,
    said internal middle section being shaped as a container to form an internal container,
    said holding sockets communicating with said internal container,
    said internal container being sized such that dental instruments placed in the sockets project above said top section and approximately to a bottom internal surface of said internal container,
    said internal container having a suction port and a drainage port,
    said suction port having means to connect said means to drain said internal container, and
    said internal drainage port being positioned to open into said sterilizing container.

2. The sterilizing container of claim 1 wherein, said top section substantially above the projection on the bottom surface has a lowered profile defining a second well, adapted to be vertically aligned with a water tap spout and which accommodates a rinsing, and an outlet hole located in said second well.

3. The sterilizing container of claim 2, wherein said suction port located to one side of said internal container to accommodate a quick coupler for connection to suction means that constitute part of the surgery equipment, and
    said suction port being vertically aligned with a corresponding opening in the bottom section by which passage is afforded to the coupler.

4. The sterilizing container of claim 1 wherein, direct discharge occurs through said suction port which is positioned to one side of the internal container and coinciding with a quick coupler connected to said bottom section, said quick coupler being adapted for attachment to a tube connected with suction means that constitute a part of the surgery environment.

5. The sterilizing container of claim 1 wherein, said top and bottom sections are disposed facing one another, the middle section is fitted into the bottom section and the top section is fitted over the middle section, and sealing means are located between the three sections to ensure a stable fit between the middle section and the bottom section.

6. The sterilizing container of claim 5 wherein the base of the middle section is embodied with a plurality of essentially radial channels, each terminating at a point coinciding with a respective socket in the top section, that serve to carry away liquid ejected from the instruments.

7. The sterilizing container of claim 5 wherein the bottom section exhibits two further projections located one on either side of the bottom projection and serving to embrace the support which flanks a dental chair.

* * * * *